United States Patent
Rosen et al.

(10) Patent No.: US 7,645,893 B2
(45) Date of Patent: Jan. 12, 2010

(54) HIGHLY SOLUBLE FERROCENYL COMPOUNDS

(75) Inventors: Robert K. Rosen, Lafayette, CA (US); Melissa D. Tankersley, Houston, TX (US)

(73) Assignee: Dow Global Technologies, Inc., Midland, MI (US)

( * ) Notice: Subject to any disclaimer, the term of this patent is extended or adjusted under 35 U.S.C. 154(b) by 166 days.

(21) Appl. No.: 11/666,941

(22) PCT Filed: Oct. 25, 2005

(86) PCT No.: PCT/US2005/038070

§ 371 (c)(1),
(2), (4) Date: May 2, 2007

(87) PCT Pub. No.: WO2006/052427

PCT Pub. Date: May 18, 2006

(65) Prior Publication Data

US 2008/0097056 A1 Apr. 24, 2008

Related U.S. Application Data

(60) Provisional application No. 60/625,693, filed on Nov. 5, 2004.

(51) Int. Cl.
- C07F 5/02 (2006.01)
- C07F 17/02 (2006.01)
- C08F 4/64 (2006.01)
- C08F 4/642 (2006.01)
- C08F 4/646 (2006.01)
- C08F 4/6592 (2006.01)
- C08F 4/72 (2006.01)
- B01J 31/12 (2006.01)
- B01J 31/14 (2006.01)

(52) U.S. Cl. .............. 556/7; 556/143; 502/103; 502/113; 502/152; 502/154; 526/113; 526/133; 526/134; 526/160; 526/161; 526/943

(58) Field of Classification Search ............. 502/103, 502/152, 113, 154; 526/160, 113, 133, 134, 526/161, 943; 556/7, 143
See application file for complete search history.

(56) References Cited

U.S. PATENT DOCUMENTS

| | | |
|---|---|---|
| 4,575,544 A | 3/1986 | Rooney et al. |
| 5,132,380 A | 7/1992 | Stevens et al. |
| 5,153,157 A | 10/1992 | Hlatky et al. |
| 5,189,192 A | 2/1993 | LaPointe et al. |
| 5,198,401 A | 3/1993 | Turner et al. |
| 5,321,106 A | 6/1994 | LaPointe |
| 5,470,927 A | 11/1995 | Turner et al. |
| 5,919,983 A | 7/1999 | Rosen et al. |
| 6,121,185 A | 9/2000 | Rosen et al. |
| 2002/0132729 A1 | 9/2002 | LaPointe |

FOREIGN PATENT DOCUMENTS

| | | |
|---|---|---|
| EP | 0522581 | 1/1993 |
| EP | 1153905 | 11/2001 |

OTHER PUBLICATIONS

Dietz, et al., J. Organometalic Chemistry, 1997, vol. 545-546, pp. 67-70.
International Search Report for corresponding application PCT/US2005/038070.

*Primary Examiner*—Caixia Lu

(57) ABSTRACT

Substituted ferrocenium compounds comprising at least one pendant oleophilic substituent on at least one of the cyclopentadienyl groups and an inert, compatible, noncoordinating, anion and processes for use thereof as catalyst activators for addition polymerizations or as oxidizing agents for metal complex syntheses.

16 Claims, No Drawings

US 7,645,893 B2

HIGHLY SOLUBLE FERROCENYL COMPOUNDS

CROSS-REFERENCE STATEMENT

This application claims the benefit of U.S. Provisional Application No. 60/625,693, filed Nov. 5, 2004.

BACKGROUND OF THE INVENTION

The present invention relates to a catalyst activator, also referred to as a cocatalyst. More particularly the present invention relates to a cocatalyst particularly adapted for use in an addition polymerization process for polymerization of olefins. Such an activator is particularly advantageous for use in a continuous solution polymerization process wherein catalyst, catalyst activator, and at least one polymerizable olefin monomer are added to a reactor operating under polymerization conditions to prepare high molecular weight polyolefins.

It is previously known in the art to activate olefin polymerization catalysts, particularly such catalysts comprising Group 4 metal complexes containing delocalized π-bonded ligand groups, by the use of Bronsted acid salts capable of transferring a proton to form a cationic derivative of such Group 4 metal complex. Preferred Bronsted acid salts are such compounds containing a noncoordinating anion such as protonated ammonium, sulfonium, or phosphonium borate salts disclosed in U.S. Pat. Nos. 5,919,983, 5,198,401, 5,132,380, 5,470,927, and 5,153,157.

Additional activators for use as olefin polymerization cocatalysts activators include oxidizing materials including ferrocenium-, silver- and lead-salts of non-coordinating anions, especially perfluorinated borate anions, disclosed in U.S. Pat. No. 5,321,106 and elsewhere. Such compounds are also known to be useful in the synthesis of metal complexes through metal center oxidation, as disclosed in U.S. Pat. No. 5,189,192. Disadvantageously, however, because they are ionic compounds, such activators are extremely insoluble in aliphatic hydrocarbons and only sparingly soluble in aromatic solvents. It is desirable to conduct most polymerizations of α-olefins in aliphatic hydrocarbon solvents due to the compatibility of such solvents with the monomer and in order to reduce the aromatic hydrocarbon content of the resulting polymer product. Normally, ionic activators need to be added to such polymerizations in the form of a solution in an aromatic solvent such as toluene. The use of even a small quantity of such an aromatic solvent for this purpose is undesirable since it must be removed in a devolatilization step and separated from other volatile components, a process that adds significant cost and complexity to any commercial process.

Dietz, et al., *J. Organometallic Chemistry*, 1997, 545-546 pg. 67-70 disclosed the preparation of dialkyl substituted ferrocene compounds, in particular, dioctylferrocene. No attempt was made to form cationic derivatives from the organometallic compound.

Accordingly, it would be desirable if there were provided an oxidizing catalyst activator that could be employed in solution polymerizations that use an aliphatic solvent, including condensed α-olefin monomer. Additionally, it would be desirable if there were provided an oxidizing compound, especially an oxidizing salt of a perfluorinated borate anion for use in general metal complex syntheses employing an aliphatic solvent.

SUMMARY OF THE INVENTION

According to the present invention there is now provided a substituted ferrocenium compound corresponding to the formula: $R^+A^-$, wherein $R^+$ is a cationic, substituted ferrocenium complex, comprising at least one pendant oleophilic substituent on at least one of the cyclopentadienyl groups thereof, and $A^-$ is an inert, compatible, noncoordinating, anion.

Additionally according to the present invention there is provided a process for the addition polymerization of one or more olefin monomers comprising contacting the monomer or a mixture of monomers, optionally in the presence of an inert aliphatic, alicyclic or aromatic hydrocarbon, with a catalyst composition comprising an olefin polymerization catalyst comprising a Group 3-10 metal complex and a cocatalyst comprising a substituted ferrocenium salt compound corresponding to the formula: $R^+A^-$, wherein $R^+$ is a cationic, substituted ferrocenium complex, comprising at least one pendent oleophilic substituent on at least one of the cyclopentadienyl groups thereof, and $A^+$ is an inert, compatible, noncoordinating, anion.

In a final embodiment of the invention, there is provided a process for the synthesis of a Group 3-10 organometallic compound through the use of an organometallic oxidizing agent, characterized in that the organometallic oxidizing agent is a substituted ferrocenium salt compound corresponding to the formula: $R^+A^-$, wherein $R^+$ is a cationic, substituted ferrocenium complex, comprising at least one pendent, oleophilic substituent on at least one of the cyclopentadienyl groups thereof, and $A^-$ is an inert, compatible, noncoordinating, anion.

By the use of the foregoing substituted ferrocenium salts, improved catalyst activation and metal center oxidation processes are provided. More particularly, increased catalyst efficiency and rate of polymerization or increased rate and efficiency of metal complex formation are obtained, especially using aliphatic or cycloaliphatic solvents or diluents in such process.

DETAILED DESCRIPTION OF THE INVENTION

All reference to the Periodic Table of the Elements herein shall refer to the Periodic Table of the Elements, published and copyrighted by CRC Press, Inc., 2001. Also, any reference to a Group or Groups shall be to the Group or Groups as reflected in this Periodic Table of the Elements using the IUPAC system for numbering groups. For purposes of United States patent practice, the contents of any patent, patent application, or publication referenced herein are hereby incorporated by reference in their entirety (or the equivalent US version thereof is so incorporated by reference) especially with respect to the disclosure of synthetic techniques, raw materials, and general knowledge in the art. Unless stated to the contrary, implicit from the context, or customary in the art, all parts and percents are based on weight.

If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise, refers to the listed members individually as well as in any combination.

The catalyst activators and oxidizers of the invention are further characterized in the following manner. Preferred anions, $A^-$, are those containing a single coordination complex comprising a charge bearing metal or metalloid core which anion is capable of balancing the charge of the active catalyst species (the metal cation) which is formed when the metal complex is activated or oxidized. Also, said anion should be sufficiently labile to be displaced by olefinic, diolefinic and acetylenically unsaturated compounds or neutral Lewis bases such as ethers, amines or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially. Therefore, said single tetrasubstituted boron anions, especially borates, are preferred. Most highly preferred are borate anions containing fluorinated aromatic, especially perfluorinated aromatic ligands directly attached to a central boron atom.

Preferably the compounds according to the invention are represented by the formula: $R^+A^-$, wherein:

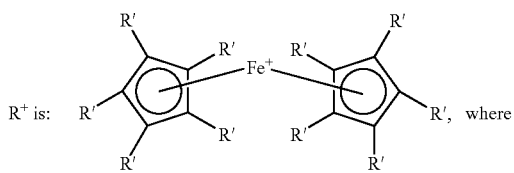

R' independently each occurrence is hydrogen, a pendant oleophilic substitutent on the central carbon ring selected from the group consisting of alkyl, cycloalkyl, alkoxy-substituted alkyl, and alkoxy-substituted cycloalkyl groups having up to 50 atoms not counting hydrogen, or two adjacent R' groups together with any remaining central ring carbon atoms form a polycyclic, fused aromatic ring system, with the proviso that in at least one occurrence, R' is a pendant substituent selected from the group consisting of alkyl, cycloalkyl, alkoxy-substituted alkyl, and alkoxy-substituted cycloalkyl groups having up to 40 atoms not counting hydrogen; and $A^-$ is a noncoordinating, compatible anion.

Examples of suitable anions of the formula $A^-$ include sterically shielded diboron anions corresponding to the formula:

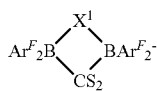

wherein:

S is alkyl, fluoroalkyl, aryl, or fluoroaryl (and where two S groups are present additionally hydrogen), $Ar^F$ is fluoroaryl, and $X^1$ is either hydrogen or halide.

Such diboron anions are disclosed in U.S. Pat. No. 5,447,895.

Additional examples of $A^-$ anions are those anions corresponding to the formula: $[M'^{k+}Q_{n'}]^-$, wherein:

k is an integer from 1 to 3;

n' is an integer from 2 to 6;

n'−k=1;

M' is an element selected from Group 13 of the Periodic Table of the Elements, preferably boron; and Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

Highly preferred anions comprising boron which are particularly useful in this invention correspond to the formula: $[BQ'_4]^-$, wherein:

B is boron in an oxidation state of 3; and

Q' is a fluorinated aryl group, more preferably a perfluorinated aryl group, and most preferably a pentafluorophenyl group.

Generally, solubility of the substituted ferrocenium salt complexes of the invention in aliphatic compounds is increased by incorporation of one or more oleophilic R' groups, preferably long chain alkyl groups, on one or more of the cyclopentadienyl groups of the ferrocenyl cation. By the term "long chain" are meant groups having from 10 to 50, preferably from 10 to 40, non-hydrogen atoms in such group, preferably in a non-branched form. Preferably such cyclopentadienyl ligands contain from 1 to 3 $C_{10-40}$ n-alkyl groups with a total of from 15 to 100 carbons, more preferably 1 or 2 $C_{10-40}$ alkyl groups and from 15 to 30 total carbons. The presence of such oleophilic groups is believed to render the substituted ferrocenyl compound more soluble in aliphatic liquids thereby improving the effectiveness in catalyst activation and metal complex formation processes. It is understood that the ferrocenium cations may comprise a mixture of oleophilic groups of differing lengths on each cyclopentadienyl ring.

Illustrative, but not limiting examples of substituted ferrocenium salts which may be used as ionic activating cocatalysts in this invention are compounds such as:

(decyl)ferrocenium tetrakis(pentafluorophenyl)borate,
(dodecyl)ferrocenium tetrakis(pentafluorophenyl)borate,
(tetradecyl)ferrocenium tetrakis(pentafluorophenyl)borate,
(octadecyl)ferrocenium tetrakis(pentafluorophenyl)borate,
di(1,2-bisdecyl)ferrocenium tetrakis(pentafluorophenyl)borate,
di(1,2-bisdodecyl)ferrocenium tetrakis(pentafluorophenyl)borate,
di(1,2-bistetradecyl)ferrocenium tetrakis(pentafluorophenyl)borate,
di(1,2-bisoctadecyl)ferrocenium tetrakis(pentafluorophenyl)borate,
di(1,3-bisdecyl)ferrocenium tetrakis(pentafluorophenyl)borate,
di(1,3-bisdodecyl)ferrocenium tetrakis(pentafluorophenyl)borate,
di(1,3-bistetradecyl)ferrocenium tetrakis(pentafluorophenyl)borate; and,
di(1,3-bisoctadecyl)ferrocenium tetrakis(pentafluorophenyl)borate.

Metal Complexes

Metal complexes that are desirably activated for use as catalysts for olefin polymerization or used in syntheses according to the invention correspond to the formula:

$$L_t M X_p X'_q,$$

wherein:

M is a metal of Group 4 of the Periodic Table of the Elements having an oxidation state of +2, +3 or +4, bound in an $\eta^5$ bonding mode to one or more L groups;

L independently each occurrence is a cyclopentadienyl-, indenyl-, tetrahydroindenyl-, fluorenyl-, tetrahydrofluorenyl-, or octahydrofluorenyl-group optionally substituted with from 1 to 8 substituents independently selected from the group consisting of hydrocarbyl, halo, halohydrocarbyl, aminohydrocarbyl, hydrocarbyloxy, dihydrocarbylamino, dihydrocarbyiphosphino, silyl, aminosilyl, hydrocarbyloxysilyl, and halosilyl groups containing up to 20 non-hydrogen atoms, or further optionally two such L groups may be joined together by a divalent substituent selected from hydrocarbadiyl, halohydrocarbadiyl, hydrocarbyleneoxy, hydrocarbyleneamino, siladiyl, halosiladiyl, and divalent aminosilane, groups containing up to 20 non-hydrogen atoms;

X independently each occurrence is a monovalent or polyvalent anionic ligand group having one or more shared or donative bonds to M, and optionally one or more shared or donative bonds to one or more L groups, said X containing up to 60 nonhydrogen atoms;

X' independently each occurrence is a neutral Lewis base ligating compound, having up to 20 atoms; and t, p, and q are 0, 1 or 2.

The activated catalyst compositions of the present invention are believed to exist in the form of a mixture of one or more cationic, zwitterionic or other catalytically active species derived from the foregoing metal complex in combination with the activator compound, or alternatively, a mixture of the metal complex or a cationic, zwitterionic or other catalytically active derivative thereof with a derivative formed by interaction of other active components of the reaction mixture with the cocatalyst or with the activated catalyst. Fully cationic or partially charge separated metal complexes, that is, zwitterionic metal complexes, have been previously disclosed in U.S. Pat. Nos. 5,470,993 and 5,486,632.

The cationic complexes are believed to correspond to the formula: $L_t M^+ X_{p-1} A^-$, wherein:

M is a Group 4 metal in the +4 or +3 formal oxidation state;

L, X, t and p are as previously defined; and $A^-$ is a noncoordinating, compatible anion derived from the activating cocatalyst.

As used herein, the recitation "noncoordinating" means an anion which either does not coordinate to the active catalyst composition or which is only weakly coordinated therewith remaining sufficiently labile to be displaced by a neutral Lewis base, including an α-olefin. A non-coordinating anion specifically refers to an anion which when functioning as a charge balancing anion in the catalyst system of this invention, does not transfer a fragment thereof to the cation portion of the active catalyst, thereby forming a neutral four coordinate metal complex and a neutral byproduct. In addition, "compatible anions" are anions which are not degraded to neutrality when the initially formed complex decomposes and are noninterfering with desired subsequent polymerizations.

Preferred X' groups are phosphines, especially trimethylphosphine, triethylphosphine, triphenylphosphine and bis (1,2-dimethylphosphino)ethane; P(OR)₃, wherein R is as previously defined; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including conjugated diene X' groups include those wherein the metal is in the +2 formal oxidation state.

Examples of metal coordination complexes used according to the present invention include the following preferred species:

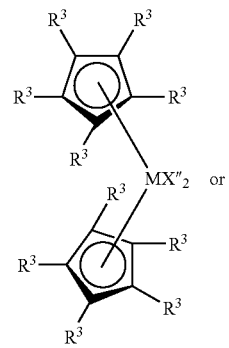

(I)

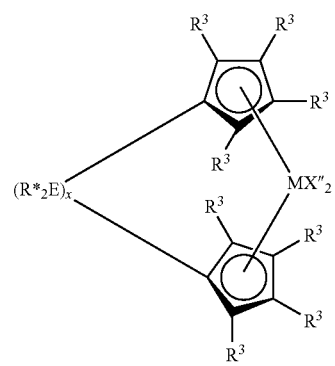

(II)

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, R* independently each occurrence is $C_{1-4}$ alkyl or phenyl, E independently each occurrence is carbon or silicon, and x is an integer from 1 to 8.

Additional examples of metal complexes used to prepare addition polymerization catalysts according to the invention include those corresponding to the formula:

$$LMX_p X'_q \qquad (III)$$

wherein L, M, X, X', p and q are as previously defined. A preferred Group 4 metal complex corresponds to the formula:

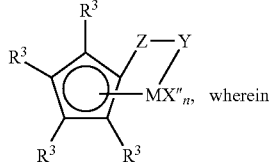

(IIIA)

M is titanium, zirconium or hafnium in the +2, +3 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups are joined together forming a polycyclic fused ring system;

each X" is a halo, hydrocarbyl, hydrocarbyloxy, hydrocarbylamino, or silyl group, said group having up to 20 nonhydrogen atoms, or two X" groups together form a neutral $C_{5-30}$ conjugated diene or a divalent derivative thereof;

Y is —O—, —S—, —NR*—, —PR*—;

Z is $SiR*_2$, $CR*_2$, $SiR*_2SiR*_2$, $CR*_2CR*_2$, $CR*$=$CR*$, $CR*_2SiR*_2$, or $GeR*_2$, wherein R* is as previously defined, and n is an integer from 1 to 3.

Most preferred Group 4 metal coordination complexes used according to the present invention are complexes corresponding to the formula:

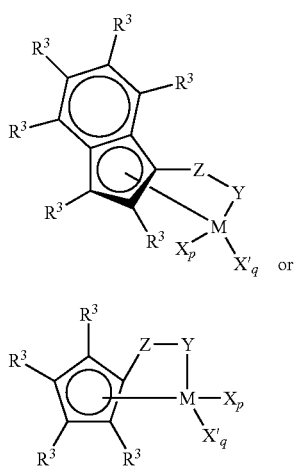

(IIIB)

(IIIC)

wherein:

$R^3$ independently each occurrence is a group selected from hydrogen, hydrocarbyl, halohydrocarbyl, silyl, germyl and mixtures thereof, said group containing up to 20 nonhydrogen atoms;

M is titanium, zirconium or hafnium;

Z, Y, X and X' are as previously defined;

p is 0, 1 or 2; and q is zero or one;

with the proviso that:

when p is 2, q is zero, M is in the +4 formal oxidation state, and X is an anionic ligand selected from the group consisting of halide, hydrocarbyl, hydrocarbyloxy, di(hydrocarbyl) amido, di(hydrocarbyl)phosphido, hydrocarbylsulfido, and silyl groups, as well as halo-, di(hydrocarbyl)amino-, hydrocarbyloxy- and di(hydrocarbyl)-phosphino-substituted derivatives thereof, said X group having up to 20 nonhydrogen atoms, when p is 1, q is zero, M is in the +3 formal oxidation state, and X is a stabilizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

Additional examples of suitable metal complexes for use in the present invention include Group 4 metal derivatives, especially hafnium derivatives of hydrocarbylamine substituted heteroaryl compounds of the formula $R^1HN$—T—$R^2$ (IV), especially complexes corresponding to the formula:

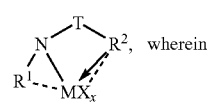

(IVA)

$R^1$ is selected from alkyl, cycloalkyl, heteroalkyl, cycloheteroalkyl, aryl, and inertly substituted derivatives thereof containing from 1 to 30 atoms not counting hydrogen;

T is a divalent bridging group of from 1 to 20 atoms other than hydrogen, preferably a mono- or di-$C_{1-20}$ hydrocarbyl substituted methylene or silane group, and $R^2$ is a heteroaryl group containing Lewis base functionality containing up to 40 atoms, not counting hydrogen, especially a pyridin-2-yl- or substituted pyridin-2-yl group, and in the metal complex, M is the Group 4 metal, preferably hafnium, X is an anionic, neutral or dianionic ligand group, x is a number from 0 to 5 indicating the number of such X groups, and bonds, optional bonds and electron donative interactions are represented by lines, dotted lines and arrows respectively.

Preferred complexes of formula IV are those wherein ligand formation results from hydrogen elimination from the amine group and optionally from the loss of one or more additional groups, especially from $R^2$. In addition, electron donation from the Lewis basic, heteroaryl functionality, preferably an electron pair, provides additional stability to the metal center. Examples of the foregoing metal complexes correspond to the formula:

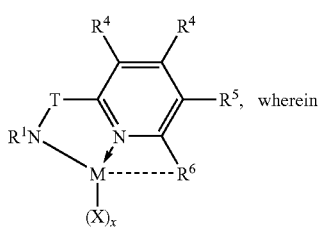

(IVA¹)

M, X, x, R$^1$ and T are as previously defined,

R$^4$, R$^5$ and R$^6$ independently each occurrence are hydrogen, halo, or an alkyl, cycloalkyl, heteroalkyl, heterocycloalkyl, aryl, or silyl group of up to 20 atoms not counting hydrogen, or adjacent R$^4$, R$^5$ or R$^6$ groups may be joined together thereby forming fused ring derivatives, and bonds, optional bonds and electron pair donative interactions are represented by lines, dotted lines and arrows respectively.

More preferred examples of the foregoing metal complexes correspond to the formula:

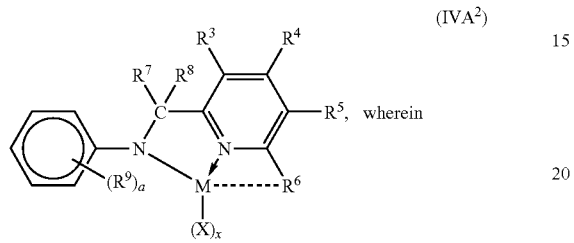

(IVA$^2$)

M, X, x, R$^1$ and T are as previously defined,

R$^3$, R$^4$, R$^5$ and R$^6$ are as previously defined, preferably R$^3$, R$^4$, and R$^5$ are hydrogen, or C$_{1-4}$ alkyl, and R$^6$ is C$_{6-20}$ aryl, most preferably naphthalenyl;

R$^9$ independently each occurrence is C$_{1-4}$ alkyl, and a is 1-5, most preferably R$^9$ in two ortho-positions is isopropyl or t-butyl;

R$^7$ and R$^8$ independently each occurrence are hydrogen or a C$_{1-20}$ alkyl or aryl group, most preferably one of R$^7$ and R$^8$ is hydrogen and the other is a C$_{6-20}$ aryl group, especially a fused polycyclic aryl group, most preferably an anthracenyl group, and bonds, optional bonds and electron pair donative interactions are represented by lines, dotted lines and arrows respectively.

Highly preferred metal complexes of formula (IV) for use herein correspond to the formula:

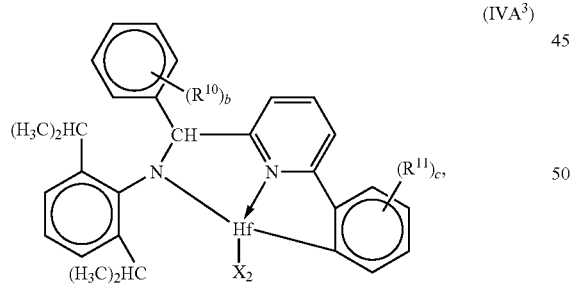

(IVA$^3$)

wherein X each occurrence is halide, N,N-dimethylamido, or C$_{1-4}$ alkyl, and preferably each occurrence X is methyl;

R$^{10}$ independently each occurrence is C$_{1-20}$ alkyl or aryl, or two adjacent R$^{10}$ groups are joined together thereby forming a ring, and b is 1-5; and R$^{11}$ independently each occurrence is C$_{1-20}$ alkyl or aryl, or two adjacent R$^{11}$ groups are joined together thereby forming a ring, and c is 1-5.

Most highly preferred examples of metal complexes of formula (IV) for use according to the present invention are complexes of the following formulas:

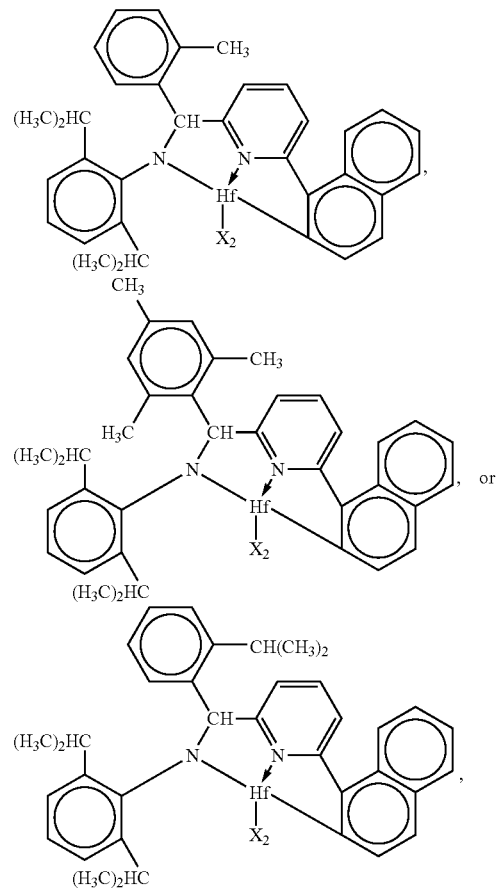

wherein X each occurrence is halide, N,N-dimethylamido, or C$_{1-4}$ alkyl, and preferably each occurrence X is methyl.

Additional suitable Group 4 metal complexes include bis (hydroxyarylaryloxy) compounds, especially hafnium derivatives of bis(hydroxyarylaryloxy) compounds of the formula: (HOAr$^1$O)$_2$T$^1$; wherein:

T$^1$ is a divalent bridging group of from 2 to 20 atoms not counting hydrogen; and Ar$^1$ independently each occurrence is a C$_{6-20}$ arylene or inertly substituted arylene group.

Preferably, such complexes correspond to the formula (V):

(V)

T$^2$ is a divalent bridging group of from 2 to 20 atoms not counting hydrogen, preferably a substituted or unsubstituted, C$_{3-6}$ alkylene group; and Ar$^2$ independently each occurrence is an arylene or an alkyl- or aryl-substituted arylene group of from 6 to 20 atoms not counting hydrogen;

M is a Group 4 metal, preferably hafnium;

X independently each occurrence is an anionic, neutral or dianionic ligand group;

x is a number from 1 to 5 indicating the number of such X groups; and bonds and electron donative interactions in this and all other formulas depicted herein are represented by lines and arrows respectively.

Preferred examples of metal complexes of formula (V) correspond to the formula:

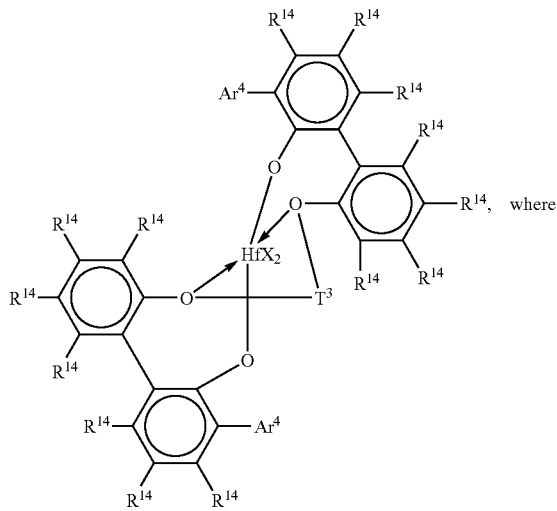

(VA)

, where

Ar$^4$ is C$_{6-20}$ aryl or inertly substituted derivatives thereof, especially 3,5-di(isopropyl)phenyl, 3,5-di(isobutyl)phenyl, dibenzo-1H-pyrrole-1-yl, or anthracen-5-yl, and T$^3$ independently each occurrence is C$_{3-6}$ alkylene or an inertly substituted derivative thereof;

R$^{14}$ independently each occurrence is hydrogen, halo, hydrocarbyl, trihydrocarbylsilyl, or trihydrocarbylsilylhydrocarbyl of up to 50 atoms not counting hydrogen; and X, independently each occurrence is halo or a hydrocarbyl or trihydrocarbylsilyl group of up to 20 atoms not counting hydrogen, or 2 X groups together are a divalent derivative of the foregoing hydrocarbyl or trihydrocarbylsilyl groups.

Especially preferred compounds of formula (V) correspond to the formula:

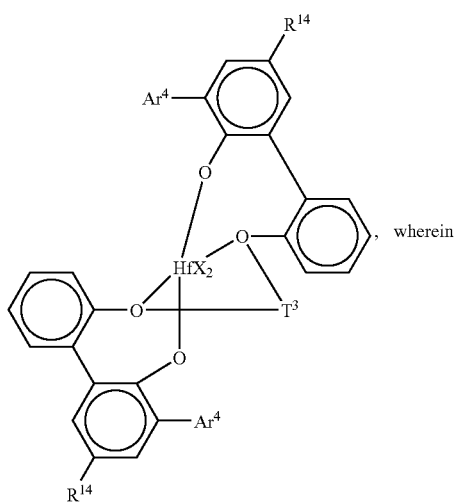

(VB)

, wherein

Ar$^4$ is 3,5-di(isopropyl)phenyl, 3,5-di(isobutyl)phenyl, dibenzo-1H-pyrrole-1-yl, or anthracen-5-yl, R$^{14}$ is hydrogen, halo, or C$_{1-4}$ alkyl, especially methyl T$^3$ is propan-1,3-diyl or butan-1,4-diyl, and X is chloro, methyl or benzyl.

A most highly preferred metal complex of formula (V) corresponds to the formula:

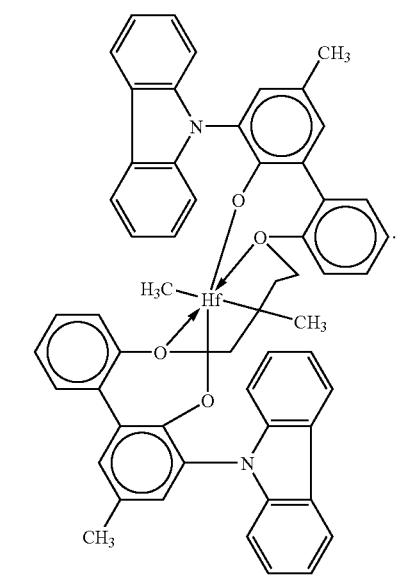

The foregoing bis(hydroxyarylaryloxy) complexes are conveniently prepared by standard mutilation and ligand exchange procedures involving a source of the Group 4 metal and the neutral bis(hydroxyarylaryloxy) compound as disclosed in US-A-2004/0005984, published Jan. 8, 2004, US-A-2004/0010103, published Jan. 15, 2004, and US-A-2004/0014950, published Jan. 22, 2004. Other techniques to prepare the foregoing metal complexes may be used as well.

Metal complexes that are suitably oxidized during synthesis of further derivatives include any complex wherein the metal is in an oxidation state that can be raised by use of an oxidizing agent. The oxidation in such case occurs at the metal center leaving a neutral metal complex product rather than a cationic product, and is referred to as a metal center oxidation rather than a molecular oxidation. Preferred metal complexes are derivatives of Group 4 metals wherein the metal is in the +2 or +3 formal oxidation state.

The following embodiments of the invention are provided as specific enablement for the appended claims. Accordingly, the present invention provides:

1. A substituted ferrocenium compound corresponding to the formula: R$^+$A$^-$, wherein R$^+$ is a cationic, substituted ferrocenium complex, comprising at least one pendant oleophilic substituent on at least one of the cyclopentadienyl groups thereof, and A$^-$ is an inert, compatible, noncoordinating, anion.

2. A substituted ferrocenium compound according to embodiment 1, wherein:

R⁺ is: 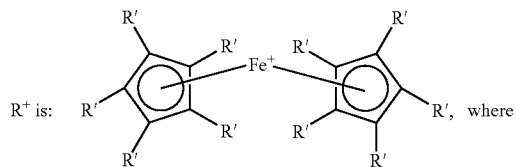 where

R' independently each occurrence is hydrogen, a pendant oleophilic substitutent on the central carbon ring selected from the group consisting of alkyl, cycloalkyl, alkoxy-substituted alkyl, and alkoxy-substituted cycloalkyl groups having up to 50 atoms not counting hydrogen, or two adjacent R' groups together with any remaining central ring carbon atoms form a polycyclic, fused aromatic ring system, with the proviso that in at least one occurrence, R' is a pendant substituent selected from the group consisting of alkyl, cycloalkyl, alkoxy-substituted alkyl, and alkoxy-substituted cycloalkyl groups having up to 40 atoms not counting hydrogen.

3. A substituted ferrocenium compound according to embodiment 2 wherein R' in at least one occurrence is a long chain alkyl group.

4. A substituted ferrocenium compound according to embodiment 2 wherein A⁻ corresponds to the formula: [BQ'$_4$]⁻, wherein:

B is boron in an oxidation state of 3; and

Q' is a fluorinated aryl group.

5. A substituted ferrocenium compound according to embodiment 4 wherein Q" each occurrence is a pentafluorophenyl group.

6. A substituted ferrocenium compound according to embodiment 1 which is dioctadecylferrocenium tetrakis(pentafluorophenyl)borate.

7. A process for the addition polymerization of one or more olefin monomers comprising contacting the monomer or a mixture of monomers, optionally in the presence of an inert aliphatic, alicyclic or aromatic hydrocarbon, with a catalyst composition comprising an olefin polymerization catalyst comprising a Group 3-10 metal complex and a cocatalyst according to any one of embodiments 1-6.

8. A process for the synthesis of a Group 3-10 organometallic compound through the use of an organometallic oxidizing agent, characterized in that the organometallic oxidizing agent is a substituted ferrocenium salt compound according to any one of embodiments 1-6.

EXAMPLES

The invention is further illustrated by the following example that should not be regarded as limiting of the present invention.

Example 1

Dioctadecylferrocenium tetrakis(pentafluorophenyl)borate (DODFT)

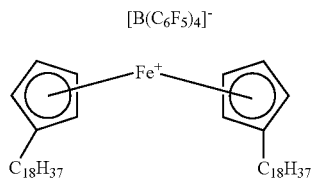

In an inert atmosphere drybox, dilithioferrocene bis(T-MEDA) (1.41 g, 3.28 mmol) is suspended in 25 mL of toluene in a 100 mL round bottomed flask. Bromooctadecane (2.24 mL, 6.55 mmol) is added and the mixture heated to reflux overnight. The mixture is then cooled and the volatile materials removed under vacuum. The dark solids are slurried in pentane and filtered with diatomaceous earth filter aid. The filtrate is dried under vacuum to leave a dark oil. After dilution in methanol, the mixture is filtered. The waxy solid is recovered from the filter and dried under vacuum.

The dioctadecylferrocene (0.258 g, 0.37 mmol) is weighed into a 250 m glass flask. Concentrated sulfuric acid (3 mL) is added and the mixture stirred for 45 minutes, during which time the color turns to dark green. Water (50 mL) is added and the mixture stirred for 5 minutes, then poured into an aqueous solution of potassium tetrakis(pentafluorophenyl)borate (0.268 g, 0.37 mol), forming a grey solid. Ether (100 mL) is added and the mixture stirred, then transferred to a separatory funnel, where the aqueous layer is removed an discarded. The ether layer is washed with water and 30 percent aqueous NaCl, with the aqueous layer being discarded. The remaining ether solution is stirred over MgSO$_4$ for 2 hours, filtered, and transferred to a clean glass bottle. The bottle is capped with a septum and the solution sparged thoroughly with N$_2$. The bottle is taken into the drybox, the solution is transferred to a clean glass receptacle and volatiles are removed under vacuum.

Polymerization

A stirred 3.8 L, autoclave reactor is charged with mixed alkanes, varying quantities of 1-octene, 10 mmol of hydrogen, methylalumoxane (10/1 based on catalyst as a scavenger). After heating to 130° C., the reactor is saturated with ethylene at 3.4 MPa. The Group 4 metal complex (t-butylamido)dimethyl(2-methyl-s-indacen-1-yl)titanium(II) 1,3-pentadiene (CAS numbers 199876-48-7, 200074-30-2) and cocatalyst (trispentafluorophenylborane (FAB) or dioctadecylferrocenium tetrakis(pentafluorophenyl)borate (DODFT) are combined in hexane solvent in a drybox and transferred by syringe to the reactor over approximately 3 minutes using N$_2$. The polymerization is allowed to continue while feeding ethylene on demand to maintain the internal pressure at 3.4 MPa. After 10 minutes polymerization, the reaction is terminated and the reactor contents discharged. Efficiency is calculated based on total grams of ethylene consumed. Results are contained in Table 1.

TABLE 1

| Run | Catalyst (µmol) | Cocatalyst | MAO (µmol) | 1-octene (g) | $C_2H_4$ (g) | Eff.[1] |
|---|---|---|---|---|---|---|
| A* | 1.25 | FAB | 12.5 | 251 | 69.3 | 55.4 |
| B* | " | " | " | " | 69.0 | 55.2 |
| 1 | " | DODFT[2] | " | " | 80.2 | 64.2 |
| 2 | 0.75 | " | 7.5 | 252 | 69.6 | 92.8 |

*Comparative, not an example of the invention
[1]grams ethylene/µmol titanium

As may be seen by reference to the results contained in Table 1, improved catalyst efficiency is observed when the compounds of the present invention are employed as a cocatalyst in an olefin polymerization compared to the use of trispentafluorophenylborane.

The invention claimed is:

1. A substituted ferrocenium compound corresponding to the formula: $R^+A^-$, wherein $R^+$ is a cationic, substituted ferrocenium complex, comprising at least one pendant oleophilic substituent on at least one of the cyclopentadienyl groups thereof, and $A^-$ is an inert, compatible, noncoordinating, anion wherein the ferrocenium compound is selected from the group consisting of:
   (decyl)ferrocenium tetrakis(pentafluorophenyl)borate,
   (dodecyl)ferrocenium tetrakis(pentafluorophenyl)borate,
   (tetradecyl)ferrocenium tetrakis(pentafluorophenyl)borate,
   (octadecyl)ferrocenium tetrakis(pentafluorophenyl)borate,
   di(1,2-bisdecyl)ferrocenium tetrakis(pentafluorophenyl)borate,
   di(1,2-bisdodecyl)ferrocenium tetrakis(pentafluorophenyl)borate,
   di(1,2-bistetradecyl)ferrocenium tetrakis(pentafluorophenyl)borate,
   di(1,2-bisoctadecyl)ferrocenium tetrakis(pentafluorophenyl)borate,
   di(1,3-bisdecyl)ferrocenium tetrakis(pentafluorophenyl)borate,
   di(1,3-bisdodecyl)ferrocenium tetrakis(pentafluorophenyl)borate,
   di(1,3-bistetradecyl)ferrocenium tetrakis(pentafluorophenyl)borate; and,
   di(1,3-bisoctadecyl)ferrocenium tetrakis(pentafluorophenyl)borate.

2. A process for the addition polymerization of one or more olefin monomers comprising contacting the monomer or a mixture of monomers, optionally in the presence of an inert aliphatic, alicyclic or aromatic hydrocarbon, with a catalyst composition comprising an olefin polymerization catalyst comprising a Group 3-10 metal complex and a cocatalyst according to claim 1.

3. A process for the synthesis of a Group 3-10 organometallic compound through the use of an organometallic oxidizing agent, characterized in that the organometallic oxidizing agent is a substituted ferrocenium salt compound according to claim 1.

4. The process of claim 2 wherein the metal complex corresponds to the formula: $L_tMX_pX'_q$, wherein M is a metal of Group 4 of the Periodic Table of the Elements having an oxidation state of +2, +3 or +4, bound in an $\eta^5$ bonding mode to one or more L groups;

L independently each occurrence is a cyclopentadienyl-, indenyl-, tetrahydroindenyl-, fluorenyl-, tetrahydrofluorenyl-, or octahydrofluorenyl-group optionally substituted with from 1 to 8 substituents independently selected from the group consisting of hydrocarbyl, halo, halohydrocarbyl, aminohydrocarbyl, hydrocarbyloxy, dihydrocarbylamino, dihydrocarbylphosphino, silyl, aminosilyl, hydrocarbyloxysilyl, and halosilyl groups containing up to 20 non-hydrogen atoms, or further optionally two such L groups may be joined together by a divalent substituent selected from hydrocarbadiyl, halohydrocarbadiyl, hydrocarbyleneoxy, hydrocarbyleneamino, siladiyl, halosiladiyl, and divalent aminosilane, groups containing up to 20 non-hydrogen atoms;

X independently each occurrence is a monovalent or polyvalent anionic ligand group having one or more shared or donative bonds to M, and optionally one or more shared or donative bonds to one or more L groups, said X containing up to 60 nonhydrogen atoms;

X' independently each occurrence is a neutral Lewis base ligating compound, having up to 20 atoms; and t, p, and q are 0, 1 or 2.

5. The process of claim 2 wherein the metal complex corresponds to

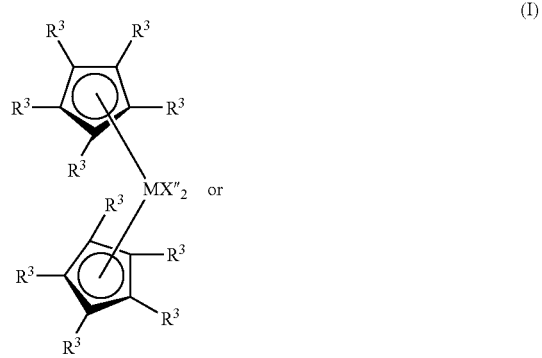

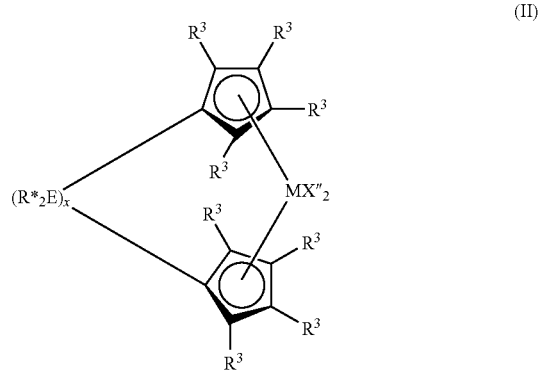

wherein:

M is titanium, zirconium or hafnium, preferably zirconium or hafnium, in the +2 or +4 formal oxidation state;

$R^3$ each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system, X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, $R^*$ independently each occurrence is $C_{1-4}$ alkyl or phenyl, E independently each occurrence is carbon or silicon, and x is an integer from 1 to 8.

6. The process of claim 2 wherein the metal complex corresponds to

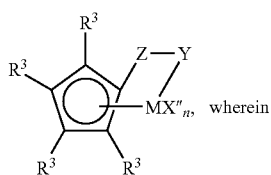
(IIIA)

M is titanium, zirconium or hafnium in the +2, +3 or +4 formal oxidation state;

$R^3$ each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups are joined together forming a polycyclic fused ring system;

each X" is a halo, hydrocarbyl, hydrocarbyloxy, hydrocarbylamino, or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein $R^*$ $R^*$ independently each occurrence is $C_{1-4}$ alkyl or phenyl; and, n is an integer from 1 to 3.

7. The process of claim 2 wherein the metal complex corresponds to

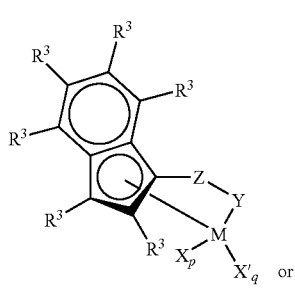
(IIIB)

or

-continued

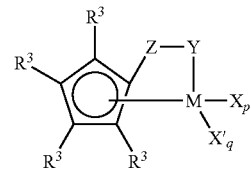
(IIIC)

wherein:

$R^3$ independently each occurrence is a group selected from hydrogen, hydrocarbyl, halohydrocarbyl, silyl, germyl and mixtures thereof, said group containing up to 20 nonhydrogen atoms;

M is titanium, zirconium or hafnium;

X independently each occurrence is a monovalent or polyvalent anionic ligand group having one or more shared or donative bonds to M, and optionally one or more shared or donative bonds to one or more L groups, said X containing up to 60 nonhydrogen atoms;

X' independently each occurrence is a neutral Lewis base ligating compound, having up to 20 atoms;

Y is —O—, —S—, —NR*—, —PR*—;

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein $R^*$ $R^*$ independently each occurrence is $C_{1-4}$ alkyl or phenyl; and, p is 0, 1 or 2; and q is zero or one;

with the proviso that:

when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)-phosphino-substituted derivatives thereof, said X group having up to 20 nonhydrogen atoms, when p is 1, q is zero, M is in the +3 formal oxidation state, and X is a stabilizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

8. The process of claim 2 wherein the metal complex corresponds to

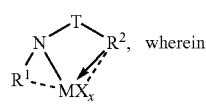
(IVA)

$R^1$ is selected from alkyl, cycloalkyl, heteroalkyl, cycloheteroalkyl, aryl, and inertly substituted derivatives thereof containing from 1 to 30 atoms not counting hydrogen;

T is a divalent bridging group of from 1 to 20 atoms other than hydrogen;

$R^2$ is a heteroaryl group containing Lewis base functionality containing up to 40 atoms, not counting hydrogen;

M is a Group 4 metal;

X is an anionic, neutral or dianionic ligand group;

x is a number from 0 to 5 indicating the number of X groups; and, bonds, optional bonds and electron donative interactions are represented by lines, dotted lines and arrows respectively.

9. The process of claim 2 wherein the metal complex corresponds to

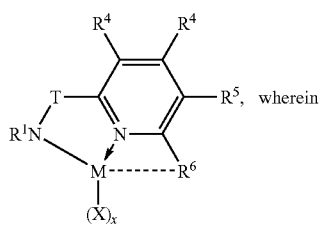

(IVA$^1$)

wherein $R^1$ is selected from alkyl, cycloalkyl, heteroalkyl, cycloheteroalkyl, aryl, and inertly substituted derivatives thereof containing from 1 to 30 atoms not counting hydrogen;

T is a divalent bridging group of from 1 to 20 atoms other than hydrogen;

M is a Group 4 metal;

X is an anionic, neutral or dianionic ligand group;

x is a number from 0 to 5 indicating the number of X groups;

$R^4$, $R^5$ and $R^6$ independently each occurrence are hydrogen, halo, or an alkyl; cycloalkyl, heteroalkyl, heterocycloalkyl, aryl, or silyl group of up to 20 atoms not counting hydrogen, or adjacent $R^4$, $R^5$ or $R^6$ groups may be joined together thereby forming fused ring derivatives; and, bonds, optional bonds and electron pair donative interactions are represented by lines, dotted lines and arrows respectively.

10. The process of claim 2 wherein the metal complex corresponds to

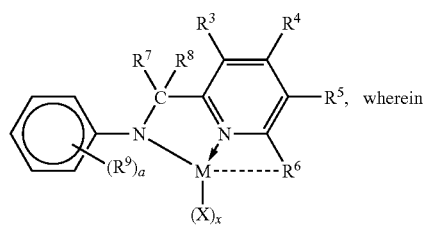

(IVA$^2$)

M is a Group 4 metal;

X is an anionic, neutral or dianionic ligand group;

x is a number from 0 to 5 indicating the number of X groups;

$R^3$, $R^4$, and $R^5$ are hydrogen or $C_{1-4}$ alkyl;

$R^6$ is $C_{6-20}$ aryl;

$R^9$ independently each occurrence is $C_{1-4}$ alkyl;

a is 1-5;

$R^7$ and $R^8$ independently each occurrence are hydrogen or a $C_{1-20}$ alkyl or aryl group;

and, bonds, optional bonds and electron pair donative interactions are represented by lines, dotted lines and arrows respectively.

11. The process of claim 2 wherein the metal complex corresponds to

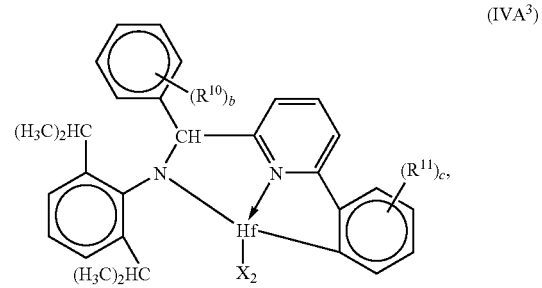

(IVA$^3$)

wherein

X each occurrence is halide, N,N-dimethylamido, or $C_{1-4}$ alkyl;

$R^{10}$ independently each occurrence is $C_{1-20}$ alkyl or aryl, or two adjacent $R^{10}$ groups are joined together thereby forming a ring, and b is 1-5; and $R^{11}$ independently each occurrence is $C_{1-20}$ alkyl or aryl, or two adjacent $R^{11}$ groups are joined together thereby forming a ring, and c is 1-5.

12. The process of claim 2 wherein the metal complex corresponds to:

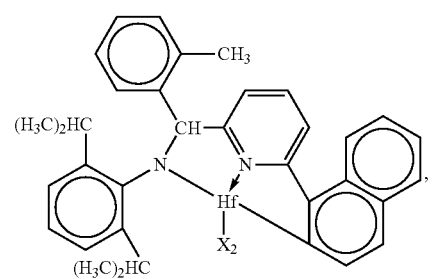

,

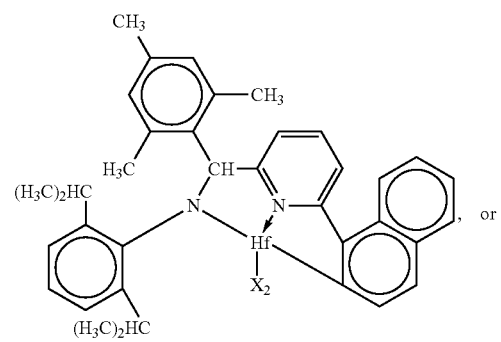

, or

-continued

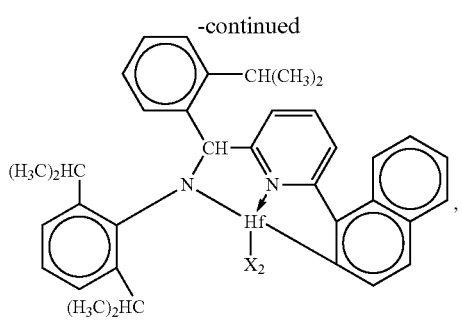

wherein X each occurrence is halide, N,N-dimethylamido, or $C_{1-4}$ alkyl.

13. The process of claim 2 wherein the metal complex corresponds to

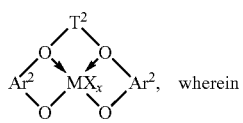
(V)

wherein $T^2$ is a divalent bridging group of from 2 to 20 atoms not counting hydrogen;

$Ar^2$ independently each occurrence is an arylene or an alkyl- or aryl-substituted arylene group of from 6 to 20 atoms not counting hydrogen;

M is a Group 4 metal;

X independently each occurrence is an anionic, neutral or dianionic ligand group;

x is a number from 1 to 5 indicating the number of X groups; and, bonds and electron donative interactions are represented by lines and arrows respectively.

14. The process of claim 2 wherein the metal complex corresponds to

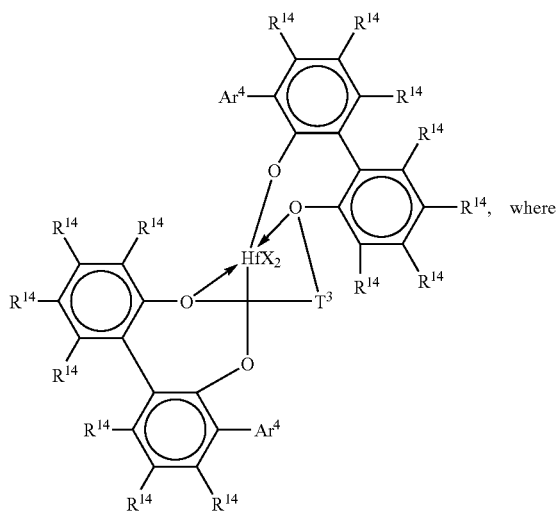
(VA)

where $Ar^4$ is $C_{6-20}$ aryl or inertly substituted derivatives thereof;

$T^3$ independently each occurrence is $C_{3-6}$ alkylene or an inertly substituted derivative thereof;

$R^{14}$ independently each occurrence is hydrogen, halo, hydrocarbyl, trihydrocarbylsilyl, or trihydrocarbylsilylhydrocarbyl of up to 50 atoms not counting hydrogen; and X, independently each occurrence is halo or a hydrocarbyl or trihydrocarbylsilyl group of up to 20 atoms not counting hydrogen, or 2 X groups together are a divalent derivative of the hydrocarbyl or trihydrocarbylsilyl groups.

15. The process of claim 2 wherein the metal complex corresponds to

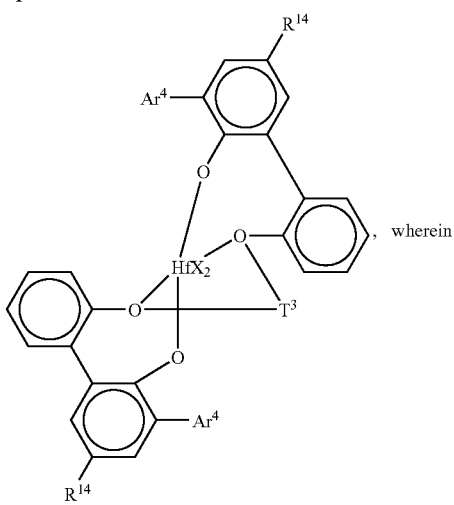
(VB)

wherein $Ar^4$ is 3,5-di(isopropyl)phenyl, 3,5-di(isobutyl)phenyl, dibenzo-1H-pyrrole-1-yl, or anthracen-5-yl;

$R^{14}$ is hydrogen, halo, or $C_{1-4}$ alkyl;

$T^3$ is propan-1,3-diyl or butan-1,4-diyl; and,

X is chloro, methyl or benzyl.

16. The process of claim 2 wherein the metal complex corresponds to

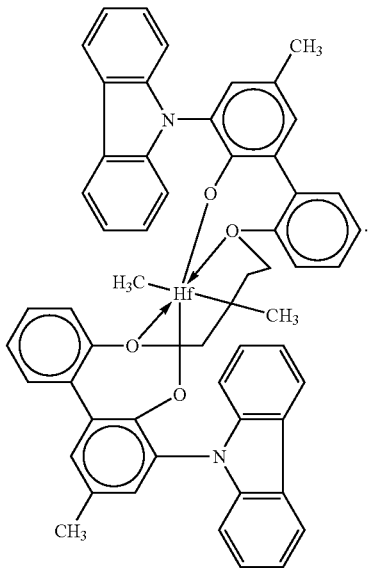

* * * * *